United States Patent [19]

Rose et al.

[11] 4,223,039
[45] Sep. 16, 1980

[54] THERAPEUTICALLY USEFUL N-PHENYLANILINE DERIVATIVES

[75] Inventors: Francis E. E. Rose; Christian J. M. Warolin; Pierre Muller, all of Paris; Paul M. P. Fabiani, Neuilly-sur-Seine; Bernard Gaudillière, Nanterre, all of France

[73] Assignee: Metabio Joullie, France

[21] Appl. No.: 20,358

[22] Filed: Mar. 14, 1979

[30] Foreign Application Priority Data

Mar. 15, 1978 [FR] France ............... 78 07443

[51] Int. Cl.$^2$ ............... C07C 101/447; A61K 31/195; A61K 31/38
[52] U.S. Cl. ............... 424/275; 424/319; 562/456; 562/457; 560/43; 549/72
[58] Field of Search ............... 562/457, 433, 456; 560/43; 260/332.3 R; 424/319, 275; 549/72

[56] References Cited

U.S. PATENT DOCUMENTS

| | | | |
|---|---|---|---|
| 3,531,467 | 9/1970 | Archer et al. | 424/244 |
| 3,642,887 | 2/1972 | Jackisch | 562/457 |
| 3,781,095 | 12/1973 | Klemm et al. | 424/319 |
| 4,034,111 | 7/1977 | Schoetenslack et al. | 424/319 |
| 4,069,344 | 1/1978 | Kauer | 560/43 |
| 4,072,705 | 2/1978 | Mieville | 549/72 |
| 4,153,718 | 5/1979 | Goudie | 424/275 |

OTHER PUBLICATIONS

Simonor et al., Chem. Abst., vol. 83, #113985g (1975).

Primary Examiner—Natalie Trousof
Assistant Examiner—James H. Reamer
Attorney, Agent, or Firm—Gordon W. Hueschen

[57] ABSTRACT

There are provided compounds of the general formula

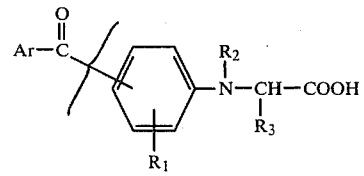

in which Ar represents a phenyl group which is unsubstituted or substituted by a halogen atom or a lower alkyl group, or represents a thienyl group, $R_1$ represents a hydrogen or halogen atom or, when the Ar—CO— grouping is in the meta-position with respect to the nitrogen atom, a lower alkyl group, $R_2$ represents a hydrogen atom, or a lower alkyl or an acyl group, and $R_3$ represents a hydrogen atom, a lower alkyl or a phenyl group and a physiologically acceptable salt thereof.

The compounds of the general formula I and their salts have therapeutic utility, especially as analgesics.

10 Claims, No Drawings

THERAPEUTICALLY USEFUL N-PHENYLANILINE DERIVATIVES

The present invention relates to new N-phenylaniline derivatives, their preparation and their therapeutical use, especially as analgesics.

According to the present invention, there are provided compounds of the general formula:

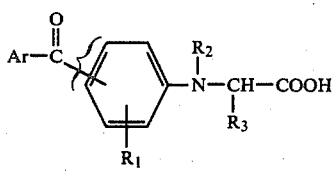

in which
- Ar represents a phenyl group which is unsubstituted or substituted by a halogen atom or a lower alkyl group, or represents a thienyl group,
- $R_1$ represents a hydrogen or halogen atom or, when the Ar—CO—grouping is in the meta-position with respect to the nitrogen atom, a lower alkyl group,
- $R_2$ represents a hydrogen atom, or a lower alkyl or an acyl group, and
- $R_3$ represents a hydrogen atom, a lower alkyl or a phenyl group, in the form of racemates or optical isomers, as well as their physiologically acceptable salts.

Suitably the Ar—CO—grouping is in the meta- or para-position with respect to the nitrogen atom.

By lower alkyl groups are meant alkyl groups having 1 to 4 carbon atoms, in particular methyl groups; by acyl groups, in particular acetyl, benzoyl and most particularly p-chlorobenzoyl groups are intended.

Amongst the physiologically acceptable salts, alkali, alkaline earth metal and the salts obtained with organic bases such as lysine are preferred.

One of the aspects of the invention may be represented by the compounds structurally most related to phenylalanine and phenylglycine and which correspond to the formula:

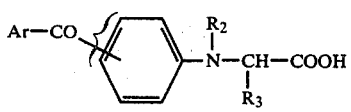

in which
- Ar represents a phenyl group, which is unsubstituted or substituted by a halogen atom or a lower alkyl group, and
- each of $R_2$ and $R_3$, which may be the same or different, represents a hydrogen atom or methyl group, as well as their physiologically acceptable salts.

The compounds of the invention may be prepared by reaction of a substituted aniline of the general formula:

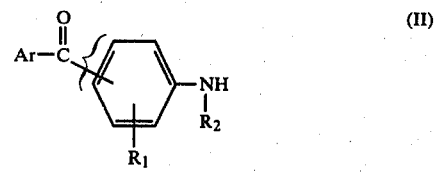

with an α-halogenated acid or ester of the general formula

in a polar solvent and in the presence of an acid acceptor, and then, if necessary, saponification of the ester obtained. There may be used for example, as polar solvent, dimethylformamide and as acid acceptor, sodium acetate or potassium carbonate. In the formulae II and III the symbols $R_1$, $R_2$, $R_3$ and Ar have the same meanings as in formula I, Hal represents a halogen atom and R represents a hydrogen atom or an alkyl group.

The substituted anilines of the formula II used as intermediates are either described in the chemical literature or may be prepared from compounds of the formula

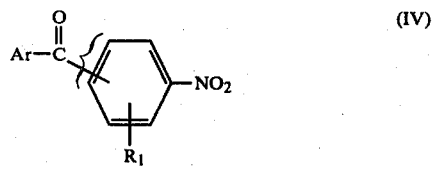

in which Ar and $R_1$ have the meanings given above, by reduction of the nitro group according to classical chemical or catalytic methods.

The compounds of the formula IV may be prepared by Friedel-Crafts reaction between nitrated benzoyl chloride and an aromatic compound ArH (Ar having the same meaning as in formula I) in the presence of a catalyst, such as aluminum chloride.

The compounds of the formula I and their salts have analgesic properties. Accordingly the invention provides a method of treating a human patient which method comprises administering thereto a compound of the formula I or a physiologically acceptable salt thereof.

The invention further provides pharmaceutical compositions which comprise a compound of the formula I or a physiologically acceptable salt thereof together with a physiologically acceptable carrier or diluent.

The following non-limiting Examples illustrate the invention:

Examples A and B illustrate the preparation of the compounds of formula IV.

EXAMPLE A

2-Methyl-3-nitro-benzophenone 23.8 g 2-Methyl-3-nitrobenzoyl chloride, prepared by the reaction of thionyl chloride with the corresponding acid, are dissolved in 100 ml anhydrous benzene. The solution is heated at the reflux of the solvent and then, with agitation, 26 g aluminum chloride are added in fractions. After the addition, the heating is maintained for 3½ hours.

The solution obtained and cooled, is poured onto ice. After extraction with chloroform, washing of the combined organic phases with dilute aqueous sodium hydroxide and then adjustment of the water to neutrality, the chloroformic phase is dried and evaporated in vacuo; the oily residue obtained crystallises at ambient temperature to give 20.1 g 2-methyl-3-nitro-benzophenone (Yield≈70%).

Melting Point (Tottoli)=36° C.

EXAMPLE B

4'-Chloro-2-methyl-3-nitro-benzophenone 12 g 2-Methyl-3-nitrobenzoyl chloride, reacted with chlorobenzene under the same conditions as in Example A, give, after identical treatment, 9 g 4'-chloro-2-methyl-3-nitrobenzophenone. (Yield=54%).

Melting Point (Tottoli)=62° C.

Examples C and D illustrate the preparation of the compounds of formula II.

EXAMPLE C

3-Amino-2-methylbenzophenone

With agitation, 20 g 2-methyl-3-nitrobenzophenone are added in fractions to a solution of 34.4 g stannous chloride in 80 ml concentrated hydrochloric acid. The mixture obtained is heated to 60° C. for 15 min; a further 20 g stannous chloride and then 100 ml alcohol at 80° C. are added.

The solution is heated to 60° C., with agitation, for 2½ hours. After cooling, dilution with water and alkalisation with dilute sodium hydroxide solution, the amine is extracted in ethyl acetate.

Evaporation in vacuo of the dried organic phase gives, after trituration of the residue obtained in cyclohexane, 15.4 g 3-amino-2-methylbenzophenone, pure according to TLC (thin layer chromatography). (Yield=88%)

Melting Point (Tottoli)=59°-60° C.

Elementary Analysis: Calculated % C=79.60; H=6.20; N=6.63. Found % C=79.81; H=6.41; N=6.55.

EXAMPLE D

3-Amino-4'-chloro-2-methylbenzophenone or 3-(4-chlorobenzoyl)-2-methylaniline 15.7 g 4'-Chloro-2-methyl-3-nitrobenzophenone are reduced under the same conditions as in Example C to give 12 g 3-amino-4'-chloro-2-methylbenzophenone. (Yield=86%) Melting Point (Tottoli)=71°-72° C.

Elementary Analysis: Calculated % C=68.44; H=4.92; N=5.70. Found % C=68.47; H=4.98; N=5.68.

EXAMPLE 1

N-[3-(4-Chlorobenzoyl)-2-methyl-phenyl]glycine (Code No. L. J 846)

To a solution of 6.1 g 3-(4-chlorobenzoyl)-2-methylaniline in 70 ml distilled dimethylformamide are added 2.2 g dry sodium acetate and then 3.4 ml ethyl bromoacetate.

The mixture obtained is agitated and heated, over an oil bath, to 90° C. for 15 hours. The dimethylformamide is then evaporated off in vacuo, then the residue obtained is taken up in a water/ether mixture. After decantation and further extraction of the aqueous phase with ether, the organic solvent is dried and evaporated in vacuo to give the crude ethyl ester of the acid prepared.

This ester is then directly saponified by dissolution in an alcoholic solution of 3 g potash and heated to 40° C. for 2 hours. After concentration to dryness and classical chemical treatment, the crude product obtained is recrystallised from benzene to give 3.5 g of acid, pure according to TLC. (Yield=46%)

Melting Point (Tottoli)=175°-176° C.

Elementary Analysis: Calculated % C=63.27; H=4.64; N=4.61. Found % C=63.41; H=4.68; N=4.62.

EXAMPLE 2

(a) N-(3-Benzoylphenyl)-alanine (Code No: L. J 874)

11 g 3-Aminobenzophenone are reacted with 7.8 ml ethyl 2-bromopropionate in 100 ml dimethylformamide in the presence of 8.6 g dry potassium carbonate, following an analogous technique to that of Example 1.

After saponification of the crude ester, followed by classical chemical treatment, the crude acid obtained is crystallised and purified by treatment with hot hexane giving 11.9 g of a slightly coloured solid.

Melting Point (Tottoli): 94°-95° C.

(Yield=76%) Melting Point (Tottoli) of the hydrochloride=142° C.

Elementary Analysis: Calculated % C=71.36; H=5.61; N=5.20. Found % C=71.45 H=5.68 N=5.17.

(b) The lysine salt of N-(3-benzoylphenyl)alanine monohydrate (Code No: L. J 843)

To a solution of 2.4 g lysine base (liberated from the hydrochloride by passage through an ion exchange resin) in water, is added N-(3-benzoyl-phenyl)-alanine obtained from 6 g of the hydrochloride monohydrate and washed with water until no chloride ions remain.

After practically complete solubilisation, the solution is filtered, the water evaporated in vacuo to give 7.2 g of slightly hydroscopic solid residue.

Elementary Analysis (monohydrate): Calculated % C=60.95; H=7.21; N=9.69. Found % C=61.23; H=6.92; N=9.65.

EXAMPLE 3

N-(3-Benzoylphenyl)-N-methyl-glycine (L. J 862)

(a) Ethyl N-(3-Benzoylphenyl)-N-methyl-glycinate 4.5 g Ethyl N-(3-benzoylphenyl)-glycinate, obtained at a 66% yield from 3-aminobenzophenone and ethyl bromoacetate by an analogous procedure to that of Example 1, are heated in the presence of 10 ml dimethyl sulphate and 2 ml water to 100° C. for 1½ hours.

After cooling, dilution with water and extraction of the aqueous phase with ether, the organic solvent is dried and evaporated in vacuo to give 3.9 g of the crude ester.

Purification is carried out by chromatography on silica with elution with chloroform. The ester thus obtained is pure according to TLC.

(b) N-(3-Benzoylphenyl)-N-methyl-glycine 1.3 g of the ester obtained above is saponified in the cold in alcoholic potash. After evaporation of the solvent and treatment, the oil obtained is triturated in a heptane/isopropyl ethyl mixture to give 0.7 g solid acid, pure according to TLC.

Melting Point (Tottoli)=98° C.
Elementary Analysis: Calculated % C=71.36; H=5.61; N=5.20. Found % C=71.46; H=5.94; N=5.23.

EXAMPLE 4

N-(3-Benzoylphenyl)-N-(4-chlorobenzoyl)-alanine
(Code No: L. J 863)

(a) 3-(4-Chlorobenzamido)-benzophenone

With agitation, 4.9 g 4-chlorobenzoyl chloride are added bit by bit to a solution, cooled to 5° C., of 5 g 3-amino-benzophenone in 60 ml dimethylacetamide, in the presence of 4.9 g triethylamine.

After the addition, the mixture is agitated at 5° C. for 1 hour, at ambient temperature for 3 hours and then poured into an aqueous hydrochloric solution.

The precipitate obtained is dried, washed with water and dried, giving 7.4 g crude product (Yield 87%). Purification may be recrystallisation from benzene.

Melting Point (Tottoli)=132°-133° C.
Elementary Analysis: Calculated % C=71.54; H=4.20; N=4.17. Found % C=71.39; H=4.25; N=3.98.

(b) Ethyl N-(3-Benzoylphenyl)-N-(4-chlorobenzoyl)alaninate 6 g 3-(4-Chlorobenzamido)-benzophenone, dissolved in 40 ml dimethylformamide, are sodified by means of 0.5 g sodium hydride added under nitrogen atmosphere.

After an hour of agitation at ambient temperature, 3.8 g ethyl 2-bromopropionate are added and the solution heated to 70° C. for 4 hours.

The cooled reaction mixture is poured into water, the precipitate separated by decantation is washed with water and dried to give 7.1 g of crude product. The ester is purified by chromatography over silica with elution with chloroform.

(c) N-(3-Benzoylphenyl)-N-(4-chlorobenzoyl)-alanine
(L. J 863)

3 g of the pure ester obtained above are saponified in hydroalcoholic potash in the cold. After evaporation of the alcohol and treatment, 1.7 g oily product is obtained. Solidification is easy by trituration in a heptane-di-isopropyl ether mixture.

Melting Point (Tottoli)=101°-102° C.
Elementary Analysis (monohydrate): Calculated % C=64.87; H=4.73; N=3.29. Found % C=64.80; H=4.81; N=3.16.

The above compounds together with compounds prepared by analogous methods to those given in the preceding Examples, are given in the following Table I. In the Table, X designates the position of the group $$Ar-\underset{\underset{O}{\|}}{C}-$$

on the phenyl nucleus.

TABLE I

| Compound No. | Code No. | Ar | X | $R_1$ | $R_2$ | $R_3$ | M.Pt.(°C.) Tottoli |
|---|---|---|---|---|---|---|---|
| 1 | * | phenyl | 3 | H | H | H | 98 hydrochloride (monohydrate) |
| 2 | | 4-Cl-phenyl | 3 | H | H | H | 143 |
| 3 | LJ 861 | phenyl | 3 | 2-CH$_3$ | H | H | 155–56 |
| 4 | LJ 871 | phenyl | 5 | 2-CH$_3$ | H | H | 133–34 |
| 5 Ex. 1 | LJ 846 | 4-Cl-phenyl | 3 | 2-CH$_3$ | H | H | 175–76 |
| 6 Ex. 2 | LJ 874 ** | phenyl | 3 | H | H | CH$_3$ | 94–95 |
| 7 | LJ 867 | 4-CH$_3$-phenyl | 3 | H | H | CH$_3$ | 131 |
| 8 | LJ 845 | 4-Cl-phenyl | 3 | H | H | CH$_3$ | 120–21 |

TABLE I-continued

| Compound No. | Code No. | Ar | X | R₁ | R₂ | R₃ | M.Pt.(°C.) Tottoli |
|---|---|---|---|---|---|---|---|
| 9 | LJ 869 | phenyl | 5 | 2-CH₃ | H | CH₃ | 115–17 |
| 10 | LJ 857 | 4-Cl-phenyl | 3 | 2-CH₃ | H | CH₃ | 128–30 |
| 11 | LJ 868 | phenyl | 3 | 4-Cl | H | CH₃ | 100–102 |
| 12 | LJ 855 | phenyl | 2 | H | H | CH₃ | 94–96 |
| 13 | LJ 854 | phenyl | 4 | H | H | CH₃ | 161–62 |
| 14 | LJ 859 | 2-thienyl | 3 | H | H | CH₃ | 122–23 |
| 15 | LJ 858 | 2-thienyl | 4 | H | H | CH₃ | 153–55 |
| 16 | LJ 864 | phenyl | 3 | H | H | C₆H₅ | 115–16 |
| 17 Ex. 3 | LJ 862 | phenyl | 3 H | CH₃ | H | | 98 |
| 18 Ex. 4 | LJ 863 | phenyl | 3 | H | 4-Cl-C₆H₄-C(=O)- | CH₃ | 101–102 |
| 19 | LJ 873 | 4-Cl-phenyl | 3 | 2-CH₃ | 4-Cl-C₆H₄-C(=O)- | H | 99–101 |

*Lysine salt: LJ 850
**Lysine salt: LJ 843.

The compounds of the invention have been subjected to pharmacological tests.

I—Acute Toxicity in Mice

The compounds have been administered at increasing doses (in geometric progression) to groups of five ♀ SWISS, EOPS, NMRI/Han mice originating from the breeding of EVIC CEBA and of mean weight 25 g.

For oral administration, they are suspended in a 10% gum arabic solution.

The LD 50s are calculated by the method of Behrens (B) and Karber (C), (Arch. Exp. Path. Pharmakol. 1935, 177, 379–388).

The number of animals surviving in the different groups is finally checked 15 days after administration of the compounds.

The results are summarised in the following Table II.

The LD 50 of aspirin is indicated by way of comparison.

TABLE II

Acute Toxicities in Mice after Oral Administration

| Compounds LJ No. | LD 50 in mg/kg |
|---|---|
| LJ 850 | 675 |
| LJ 861 | 1300 |
| LJ 846 | 1600 |
| LJ 874 | 2500 |
| LJ 843 | 3750 |
| LJ 867 | 2625 |
| LJ 845 | 1750 |
| LJ 869 | 1300 |
| LJ 857 | 1250 |
| LJ 868 | 1800 |
| LJ 855 | 1000 |
| LJ 854 | 1875 |
| LJ 859 | 2500 |
| LJ 858 | 1875 |
| LJ 864 | 2200 |
| Aspirin | 1500 |

II—Analgesic Activity in Mice

Experimental Protocol

There is used the phenylbenzoquinone test according to a technique adapted from that of Siegmund (E), Proc. Soc. Exp. Biol. Med. 1957, 95, No. 4, 729-731.

It is attempted to antagonise, by previous administration (30 minutes before) of the test compounds, the painful syndrome provoked in mice (groups of 10 animals) by interperitoneal injection of phenylbenzoquinone and characterised by intermittent contractions of the abdomen, periodic torsions of the trunk and extension of the rear paws. The number of symtoms is counted for 20 minutes after administration of the phenylbenzoquinone to the control and treated groups and the percentage protection relative to the control group calculated.

For the most interesting compounds, studied at several doses chosen in geometric progression of ratio 2, the effective doses 50% (ED 50) which reduce by 50% the effects provoked by phenylbenzoquinone are determined. These ED 50s are sorted according to their limits of confidence calculated for a probability $p=0.05$ according to the method of Litchfield (J. T.) and Wilcoxon (F. A.), J. Pharmacol. Exp. Ther. 1949, 96, 99-113.

Calculation of the therapeutic index (LD 50/ED 50) enables appreciation of the interest of the compounds.

Aspirin is studied as reference substance.

Results (Table III)

Amongst the active compounds of the invention, LJ 846, LJ 867, LJ 874 and LJ 843 show very favourable therapeutic index. LJ 843 (Lysine salt of LJ 874) possesses the advantage of being very soluble in distilled water.

TABLE III

| Compounds LJ No. | Doses in mg/kg | Percentage Protection | ED 50 in mg/kg | Therapeutic Index LD 50/ED 50 |
|---|---|---|---|---|
| LJ 850 | 33.75 | 28% | — | — |
|  | 20 | 24% |  |  |
|  | 40 | 36% |  |  |
| LJ 861 | 80 | 52% | 65 | 20 |
|  | 160 | 90% |  |  |
|  | 320 | 96% |  |  |
|  | 20 | 3% |  |  |
|  | 40 | 22% |  |  |
| LJ 871 | 80 | 34% | 120 | — |
|  | 160 | 59% |  |  |
|  | 320 | 60% |  |  |
|  | 5 | 6% |  |  |
|  | 10 | 40% |  |  |
| LJ 846 | 20 | 48% | 18 | 89 |
|  | 40 | 75% |  |  |
|  | 80 | 90% |  |  |
|  | 7.5 | 3% |  |  |
|  | 15 | 20% |  |  |
| LJ 874 | 30 | 48% | 35 | 71 |
|  | 60 | 61% |  |  |
|  | 120 | 92% |  |  |
|  | 11.75 | 30% |  |  |
|  | 23.5 | 38% |  |  |
| LJ 843 | 47 | 66% | 25 | 150 |
|  | 93.75 | 84% |  |  |
|  | 187.5 | 91% |  |  |
|  | 8.2 | 6% |  |  |
|  | 16.4 | 32% |  |  |
| LJ 867 | 32.75 | 52% | 32 | 82 |
|  | 65.5 | 70% |  |  |
|  | 131 | 92% |  |  |
|  | 262 | 97% |  |  |
| LJ 845 | 87.5 | 75% | — | — |
|  | 8.1 | 12% |  |  |
|  | 16.25 | 36% |  |  |
| LJ 869 | 32.5 | 51% | 28 | 46 |
|  | 65 | 82% |  |  |
|  | 130 | 96% |  |  |
| LJ 857 | 62.5 | 64% | — | — |
| LJ 868 | 180 | 32% | >180 | <10 |
|  | 3.1 | 10% |  |  |
|  | 6.25 | 14% |  |  |
| LJ 855 | 12.5 | 37% | 16 | 62 |
|  | 25 | 73% |  |  |
|  | 50 | 92% |  |  |
|  | 5.8 | 6% |  |  |
|  | 11.75 | 11% |  |  |
| LJ 854 | 23.5 | 25% | 32 | 58 |
|  | 47 | 84% |  |  |
|  | 93.75 | 90% |  |  |
| LJ 859 | 125 | 77% | — | — |
| LJ 858 | 93.75 | 78% | — | — |
|  | 40 | 7% |  |  |
|  | 80 | 22% |  |  |
| LJ 864 | 160 | 31% | 250 | 8,8 |
|  | 320 | 59% |  |  |
|  | 20 | 6% |  |  |
|  | 40 | 24% |  |  |
| LJ 862 | 80 | 49% | 85 | — |
|  | 160 | 78% |  |  |
|  | 320 | 89% |  |  |
| LJ 863 | 320 | 45% | — | — |
|  | 9.4 | 4% |  |  |
|  | 18.75 | 20% |  |  |
|  | 37.5 | 31% |  |  |
| Aspirin | 75 | 56% | 60 | 25 |
|  | 150 | 82% |  |  |
|  | 300 | 95% |  |  |

The compounds of the invention possess antalgic properties.

The therapeutic indications concern acute or chronic pain:

diverse rheumatic algia; athritis, periarthritis, lumbo-sciatica, arthrosis, neuralgia etc. . . .

traumatic algia, fractures, sprains, dislocations etc. . .

dental pains, facial neuralgias, headaches.

visceral pains, colic, nephritis etc. . . .

The compounds of the invention may be administered orally, rectally, parenterally, transdermally.

The daily oral posology for an adult generally comprises between 5 mg/kg and 30 mg/kg.

The preferred pharmaceutical forms are tablets, capsules, suppositories, injectable solutions, skin creams etc. . . .

Examples of Formulations:

Tablets:
- L.J. 874: 200 mg
- Excipient: starch, lactose, magnesium stearate, talc, q.s.p. 1 tablet.

Suppositories:
- L.J. 874: 400 mg
- Excipient: semi-synthetic glycerides q.s.p. 1 suppository of 2 g.

We claim:

1. Compounds of the formula

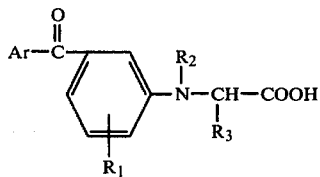

in which
- Ar is selected from the group consisting of phenyl, halophenyl, lower-alkylphenyl, and thienyl,
- $R_1$ is selected from the group consisting of hydrogen, halogen, and lower-alkyl,
- $R_2$ is selected from the group consisting of hydrogen, lower-alkyl, acetyl, benzoyl, and p-chlorobenzoyl, and
- $R_3$ is selected from the group consisting of hydrogen, lower-alkyl, and phenyl in the form of racemates or optical isomers, and physiologically-acceptable salts thereof.

2. Compounds of the formula

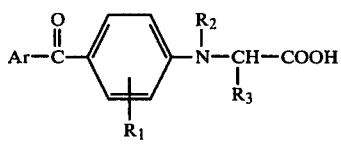

in which
- Ar is selected from the group consisting of phenyl, halophenyl, lower-alkylphenyl, and thienyl,
- $R_1$ is selected from the group consisting of hydrogen and halogen,
- $R_2$ is selected from the group consisting of hydrogen, lower-alkyl, acetyl, benzoyl, and p-chlorobenzoyl, and
- $R_3$ is selected from the group consisting of hydrogen, lower-alkyl and phenyl, in the form of racemates or optical isomers, and physiologically-acceptable salts thereof.

3. Compounds according to claim 1 of the formula

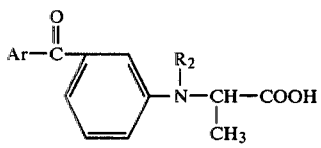

in which
- Ar is selected from the group consisting of phenyl, halophenyl, and lower-alkylphenyl, and
- $R_2$ is selected from the group consisting of hydrogen and methyl and physiologically-acceptable salts thereof.

4. A compound according to claim 1 which is N-(3-p-chlorobenzoyl-2-methyl-phenyl)-glycine or a physiologically acceptable salt thereof.

5. A compound according to claim 3 which is N-(3-p-methylbenzoyl-phenyl)alanine or a physiologically acceptable salt thereof.

6. A compound according to claim 3 which is N-(3-p-chlorobenzoyl-phenyl)-alanine or a physiologically acceptable salt thereof.

7. A compound according to claim 3 which is N-(3-benzoyl-phenyl)-alanine or a physiologically acceptable salt thereof.

8. A compound according to claim 3 which is the lysine salt of N-(3-benzoyl-phenyl)-alanine.

9. A composition useful in the treatment of acute and chronic pain in a human patient which comprises an analgesically-effective amount of a compound of claim 1 or claim 2, together with a physiologically-acceptable carrier or diluent.

10. A method for treating pain in a human patient experiencing pain which comprises administering to said patient an analgesically-effective amount of a compound of claim 1 or claim 2.

* * * * *

UNITED STATES PATENT AND TRADEMARK OFFICE
CERTIFICATE OF CORRECTION

PATENT NO. : 4,223,039

DATED : September 16, 1980

INVENTOR(S) : Francis E. E. Rose, Christian J. M. Warolin, Pierre Muller and Paul M. P. Fabiani It is certified that error appears in the above-identified patent and that said Letters Patent are hereby corrected as shown below:

[56] References Cited, U.S. PATENT DOCUMENTS, line 3; "3,781,095" should read -- 3,780,095 --

[56] References Cited, U.S. PATENT DOCUMENTS, line 4; "Schoetenslack et al." should read -- Schoetensack et al. --

[56] References Cited, U.S. PATENT DOCUMENTS, line 5; "Kauer" should read -- Karrer --

[56] References Cited, OTHER PUBLICATIONS; "Simonor et al." should read -- Simonov et al. --

Col. 5, line 20; "be recrystallisation" should read -- be by recrystallisation --

Table 1-continued, Compound No. 17, Ex. 3, columns 4th, 5th, 6th, 7th & 8th;

"3    $CH_3$    H    98"
H should read

-- 3    H    $CH_3$    H    98 --

Col. 9, line 13; "symtoms" should read -- symptoms --

Signed and Sealed this

Sixth Day of January 1981

[SEAL]

Attest:

SIDNEY A. DIAMOND

Attesting Officer

Commissioner of Patents and Trademarks